US012778867B2

(12) United States Patent
Kanemaru et al.

(10) Patent No.: US 12,778,867 B2
(45) **Date of Patent: *Nov. 3, 2026**

(54) FATTY ACID MAGNESIUM SALT PARTICLES AND COSMETIC

(71) Applicants: SHISEIDO COMPANY, LTD., Tokyo (JP); NOF CORPORATION, Tokyo (JP)

(72) Inventors: Tetsuya Kanemaru, Tokyo (JP); Mayu Kumagai, Tokyo (JP); Yuka Iwahashi, Tokyo (JP); Motoharu Kimura, Tokyo (JP); Takeshi Yoshimura, Amagasaki (JP); Mako Iwasaki, Amagasaki (JP)

(73) Assignees: SHISEIDO COMPANY, LTD., Tokyo (JP); NOF CORPORATION, Tokyo (JP)

( * ) Notice: Subject to any disclaimer, the term of this patent is extended or adjusted under 35 U.S.C. 154(b) by 336 days.

This patent is subject to a terminal disclaimer.

(21) Appl. No.: 18/043,550

(22) PCT Filed: Sep. 24, 2021

(86) PCT No.: PCT/JP2021/035141

§ 371 (c)(1),
(2) Date: Feb. 28, 2023

(87) PCT Pub. No.: WO2022/071136

PCT Pub. Date: Apr. 7, 2022

(65) Prior Publication Data

US 2023/0263713 A1 Aug. 24, 2023

(30) Foreign Application Priority Data

Sep. 30, 2020 (JP) ................................ 2020-164351

(51) Int. Cl.
*A61K 8/36* (2006.01)
*A61K 8/02* (2006.01)
(Continued)

(52) U.S. Cl.
CPC ................ *A61K 8/361* (2013.01); *A61K 8/19* (2013.01); *A61Q 1/12* (2013.01); *A61K 2800/412* (2013.01)

(58) Field of Classification Search
CPC .... A61K 8/361; A61K 8/19; A61K 2800/412; A61K 8/0245; A61Q 1/12; C07C 53/126
See application file for complete search history.

(56) References Cited

U.S. PATENT DOCUMENTS 4,960,665 A 10/1990 Elder et al.
5,283,062 A 2/1994 Elliott et al.
(Continued)

FOREIGN PATENT DOCUMENTS

CN 101891969 A 11/2010
CN 104276940 A 1/2015
(Continued)

OTHER PUBLICATIONS

English translation of JP-2016006030 (Kamiyama et al. Jan. 14, 2016), [Retrieved on May 20, 2025], Retrieved from Espacenet <https://worldwide.espacenet.com/publication Details/>.*
(Continued)

*Primary Examiner* — Sue X Liu
*Assistant Examiner* — Dongxiu Zhang
(74) *Attorney, Agent, or Firm* — Foley & Lardner LLP

(57) ABSTRACT

The invention relates to fatty acid magnesium salt particles having an aspect ratio expressed by the following formula (1) of 1.0 or more and 2.0 or less in which the fatty acid has 12 to 22 carbon atoms and in which the average thickness of the fatty acid magnesium salt particles is 250 to 600 nm.

Aspect Ratio=Major axis diameter of Particle (μm)/ Minor axis diameter of Particle (μm) formula (1)

6 Claims, 3 Drawing Sheets

(51) Int. Cl.
*A61K 8/19* (2006.01)
*A61Q 1/12* (2006.01)
*C07C 53/126* (2006.01)

(56) References Cited

U.S. PATENT DOCUMENTS

| | | | |
|---|---|---|---|
| 5,340,569 | A | 8/1994 | Elliott et al. |
| 10,639,247 | B2 | 5/2020 | Tellefsen et al. |
| 10,729,647 | B2 | 8/2020 | Green |
| 2010/0098780 | A1 | 4/2010 | Ono et al. |
| 2010/0291014 | A1 | 11/2010 | Tellefsen et al. |
| 2011/0002872 | A1 | 1/2011 | Ohashi et al. |
| 2016/0090345 | A1 | 3/2016 | Ohashi et al. |
| 2016/0143824 | A1 | 5/2016 | Niimi et al. |
| 2018/0049961 | A1 | 2/2018 | Niimi et al. |

FOREIGN PATENT DOCUMENTS

| | | | | | |
|---|---|---|---|---|---|
| EP | 2540670 | A1 | * | 1/2013 | ............... A61K 8/02 |
| EP | 4 269 472 | A1 | | 11/2023 | |
| JP | S58-49307 | A | | 3/1983 | |
| JP | S59-74200 | A | | 4/1984 | |
| JP | H06-172128 | A | | 6/1994 | |
| JP | 2000-169342 | A | | 6/2000 | |
| JP | 2002173415 | A | * | 6/2002 | |
| JP | 2004-270091 | A | | 9/2004 | |
| JP | 2007-186463 | A | | 7/2007 | |
| JP | 2008-044920 | A | | 2/2008 | |
| JP | 2016006030 | A | * | 1/2016 | ............... A61K 8/19 |
| JP | 2016-523808 | A | | 8/2016 | |
| JP | 2017-081858 | A | | 5/2017 | |
| JP | 2018-168145 | A | | 11/2018 | |
| JP | 2019-218328 | A | | 12/2019 | |

OTHER PUBLICATIONS

English translation of JP2002173415 (Takasuka et al. Jun. 21, 2022), [Retrieved on May 20, 2025], Retrieved from Espacenet <https://worldwide.espacenet.com/publication Details/>.*

Humble & me (Magnesium myristate, Jan. 22, 2019, [Retrieved on Nov. 17, 2025], Retreived online, Weblink: <https://www.humblebeeandme.com/project/magnesium-myristate/> (Year: 2019).*

International Searching Authority, "International Search Report," issued in connection with International Patent Application No. PCT/JP2021/035141, dated Dec. 7, 2021.

International Searching Authority, "Written Opinion," issued in connection with International Patent Application No. PCT/JP2021/035141, dated Dec. 7, 2021.

European Extended Search Report issued in corresponding European Patent Application No. 21875438.0 dated Nov. 28, 2024.

Office Action issued in corresponding CN Patent Application No. 202180053546.1 dated Jul. 17, 2026 (16 pages).

Xiaojun et al., "A New Process for the Preparation of Metal Soaps for Cosmetics", Household Chemical Industry China Surfactant Detergent & Cosmetics, vol. 35, No. 4, Aug. 2005, pp. 262-264.

* cited by examiner

FATTY ACID MAGNESIUM SALT PARTICLES AND COSMETIC

CROSS-REFERENCE TO RELATED APPLICATIONS

The present application claims priority under 35 U.S.C. § 371 to International Patent Application No. PCT/JP2021/035141, filed Sep. 24, 2021, which claims priority to and the benefit of Japanese Patent Application No. 2020-164351, filed on Sep. 30, 2020. The contents of these applications are hereby incorporated by reference in their entireties.

TECHNICAL FIELD

The present invention relates to novel fatty acid magnesium salt particles and a cosmetic containing the fatty acid magnesium salt particles.

BACKGROUND ART

A fatty acid magnesium salt is a metallic soap which is useful as a cosmetic additive and has been used for the purpose of improving the smoothness or the adhesion on the skin or as a dispersing agent for pigments or another purpose.

Patent Literature 1 describes a fatty acid magnesium salt which is fatty acid magnesium having 6 to 24 carbon atoms obtained by a metathesis method and in which the pH is not in the alkaline range when the fatty acid magnesium salt is dispersed in water.

Patent Literature 2 discloses that a solid powder cosmetic having excellent use feeling, formability and impact resistance is obtained when metallic soap microparticles having a specific particle size are combined with a partially cross-linked organopolysiloxane polymer.

Patent Literature 3 discloses that a solid powder cosmetic having excellent formability, impact resistance, durability and the like is obtained when a specific amount of metallic soap microparticles having a specific particle size are used.

CITATION LIST

Patent Literature

Patent Literature 1: JP-A-2007-186463
Patent Literature 2: JP-A-2018-168145
Patent Literature 3: JP-A-2000-169342

SUMMARY OF INVENTION

Technical Problem

The conventional metallic soaps, however, have room for improvement in terms of the use feeling.

A purpose of the invention is to provide a novel metallic soap and a cosmetic which have excellent use feeling.

Solution to Problem

As a result of intensive investigation to solve the problem, the present inventors have found that fatty acid magnesium salt particles having an aspect ratio within a specific range have excellent use feeling.

That is, the invention relates to the fatty acid magnesium salt particles and the cosmetic below.

[1] Fatty acid magnesium salt particles having an aspect ratio expressed by the following formula (1) of 1.0 or more and 2.0 or less, wherein the fatty acid has 12 to 22 carbon atoms, and the average thickness of the fatty acid magnesium salt particles is 250 to 600 nm:

the aspect ratio=the major axis diameter of a particle (μm)/the minor axis diameter of the particle (μm) formula (1).

[2] The fatty acid magnesium salt particles described in [1], wherein the median size is 10.0 μm to 40.0 μm.

[3] The fatty acid magnesium salt particles described in [1] or [2], wherein the particle size digest (A) expressed by the following formula (3) satisfies the relation A≤2.5:

the particle size digest $A=(D90-D10)/D50$ formula (3)

(wherein 10.0≤D50≤40.0), wherein D10 is the 10% cumulative size (μm) of the fatty acid magnesium salt particles on a volumetric basis, D50 is the median size (μm) of the fatty acid magnesium salt particles on a volumetric basis, and D90 is the 90% cumulative size (μm) of the fatty acid magnesium salt particles on a volumetric basis.

[4] The fatty acid magnesium salt particles described in any of [1] to [3], wherein the fatty acid having 12 to 22 carbon atoms is myristic acid.

[5] A cosmetic containing the fatty acid magnesium salt particles described in any of [1] to [4].

Advantageous Effects of Invention

According to the invention, fatty acid magnesium salt particles having excellent use feeling can be provided.

Moreover, according to the invention, a cosmetic having excellent use feeling can be provided because the fatty acid magnesium salt particles are contained.

DESCRIPTION OF EMBODIMENTS

Figure 1:
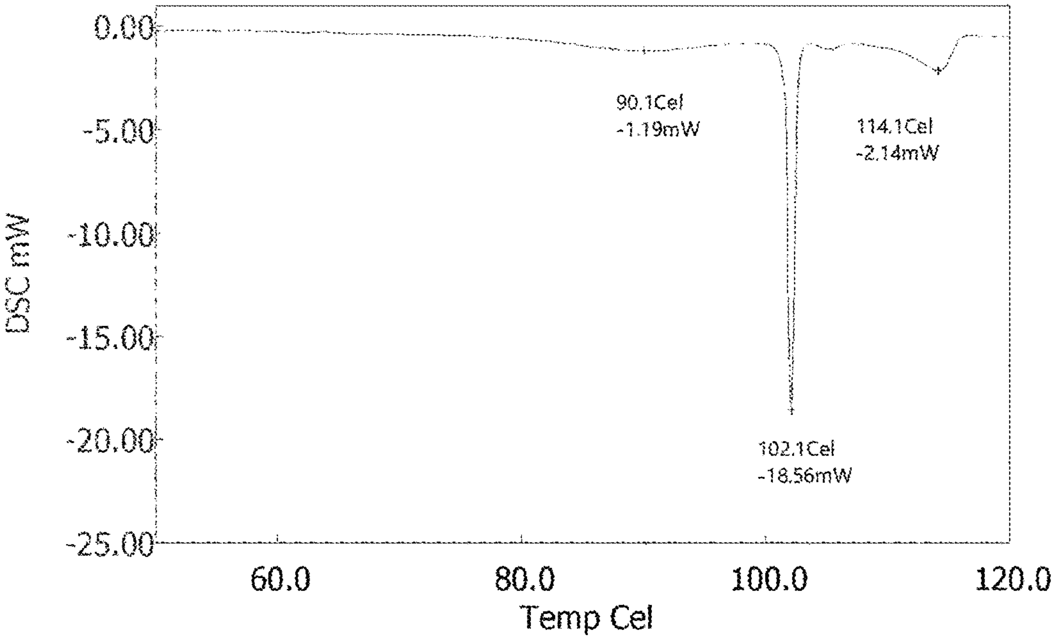
FIG. 1 is a figure showing the heat absorption graph of magnesium myristate by differential thermal analysis (DSC).
Figure 2:
FIG. 2 is a picture of the magnesium myristate of Example 1 observed under a scanning electron microscope.
Figure 3:
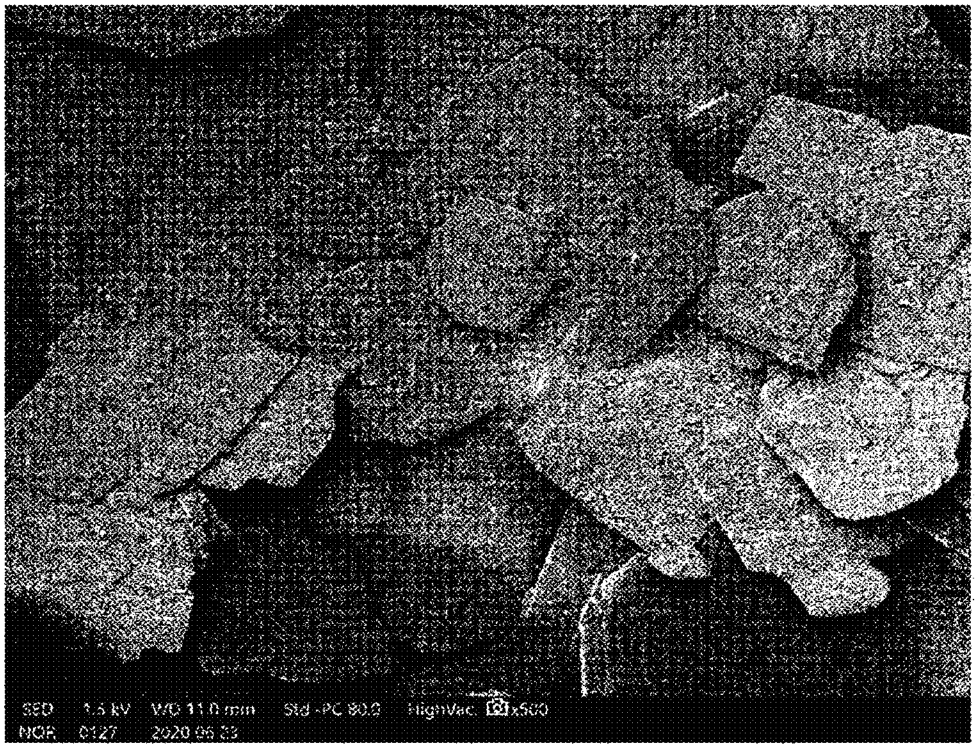
FIG. 3 is a picture of the magnesium myristate of Example 3 observed under a scanning electron microscope.
Figure 4:
FIG. 4 is a picture of the magnesium myristate of Comparative Example 1 observed under a scanning electron microscope.
Figure 5:
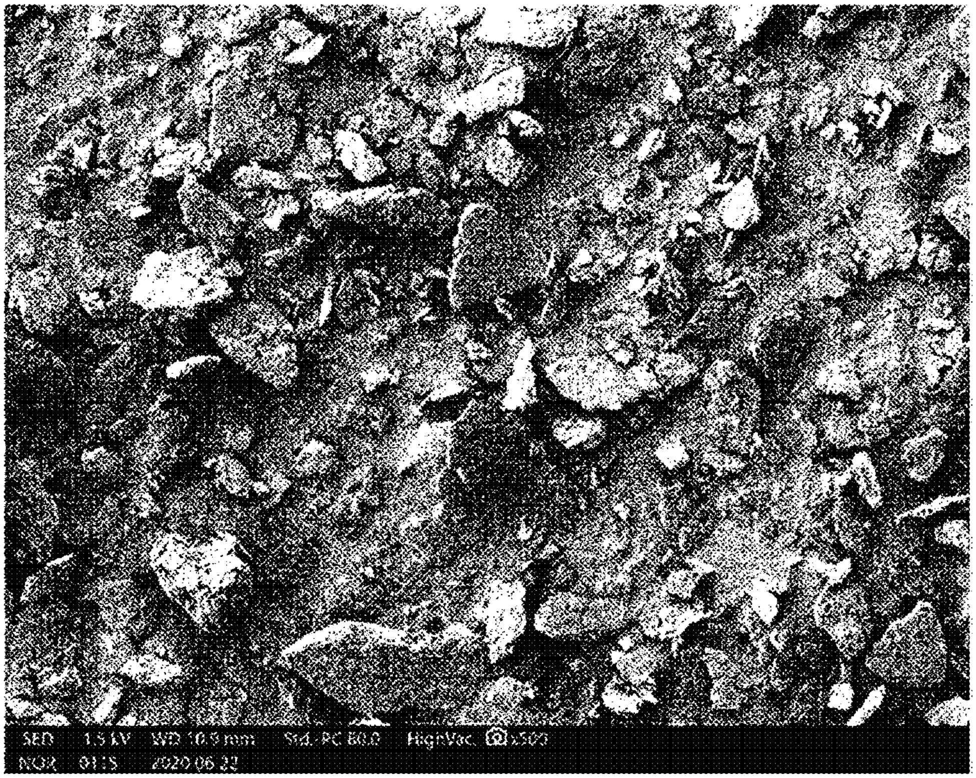
FIG. 5 is a picture of the magnesium myristate of Comparative Example 2 observed under a scanning electron microscope.
Figure 6:
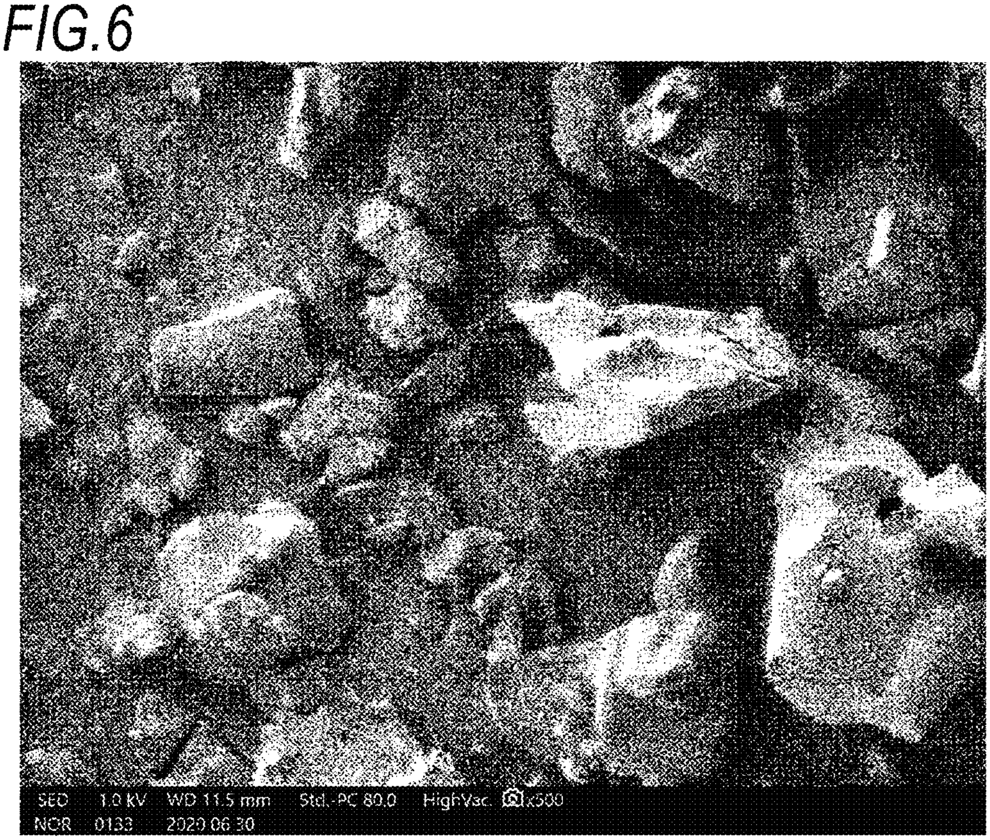
FIG. 6 is a picture of the magnesium myristate of Comparative Example 3 observed under a scanning electron microscope.

The invention is explained in further detail below.

The fatty acid magnesium salt particles of the invention are composed of a magnesium salt of a divalent fatty acid having 12 to 22 carbon atoms. The particles can be prepared by a metathesis method in which a fatty acid-alkaline compound salt obtained by reacting a monovalent alkaline compound with a fatty acid having 12 to 22 carbon atoms and a divalent magnesium salt are reacted in an aqueous solution.

The fatty acid used as the raw material of the fatty acid-alkaline compound salt is not particularly restricted as long as the fatty acid has 12 to 22 carbon atoms. That is, the fatty acid may be a naturally derived fatty acid or a synthetic fatty acid, may be a saturated fatty acid or an unsaturated fatty acid and may be a linear or branched fatty acid. The fatty acid may contain a functional group such as a hydroxyl group, an aldehyde group and an epoxy group in its structure. The fatty acid is preferably a linear saturated fatty acid.

The fatty acid has 12 or more carbon atoms and thus can give excellent use feeling to the cosmetic. Because the number of the carbon atoms is 22 or less, the fatty acid is industrially easily obtained, and the solubility of the obtained fatty acid-alkaline compound salt in water does not decrease significantly. Thus, the productivity is high. The number of the carbon atoms of the fatty acid is preferably 12 to 18, more preferably 14 (which means that the fatty acid magnesium is magnesium myristate).

Examples of the fatty acid include lauric acid, myristic acid, myristoleic acid, palmitic acid, palmitoleic acid, stearic acid, oleic acid, linoleic acid, arachic acid, behenic acid, erucic acid, hydroxystearic acid, epoxystearic acid and the like. Of these, myristic acid is preferable. When a mixed fatty acid is used, the myristic acid content of the fatty acid is preferably 50% or more, more preferably 60% or more, further preferably 70% or more.

The monovalent alkaline compound used as the raw material of the fatty acid-alkaline compound salt is a hydroxide of an alkali metal (sodium, potassium or the like), ammonia, an amine such as monoethanolamine, diethanolamine and triethanolamine or the like. Because the solubility of the resulting fatty acid-alkaline compound salt in water is high, a hydroxide of an alkali metal such as sodium and potassium is preferable.

The fatty acid-alkaline compound salt used in the invention is obtained by reacting the monovalent alkaline compound and the fatty acid generally at a temperature which is the melting point of the fatty acid or higher and at which the fatty acid does not decompose, preferably at 100° C. or lower, more preferably at 50 to 100° C., further preferably at 60 to 95° C., particularly preferably at 80 to 95° C.

The fatty acid magnesium salt particles of the invention can be obtained, for example, by reacting the fatty acid-alkaline compound salt obtained above and a magnesium salt in an aqueous solution. The magnesium salt is specifically a salt of inorganic magnesium and an inorganic acid or an organic acid. Examples of the magnesium salt include magnesium chloride, magnesium sulfate, magnesium acetate and the like. In particular, chloride of magnesium and sulfated magnesium are preferable because of the high solubility in water and the efficient reaction with the fatty acid-alkaline compound salt.

The reaction of the fatty acid-alkaline compound salt and the divalent magnesium salt is conducted specifically by preparing a magnesium salt-containing aqueous solution and a fatty acid-alkaline compound salt-containing aqueous solution separately and then mixing the solutions. For example, the reaction is conducted by adding the magnesium salt-containing aqueous solution to the fatty acid-alkaline compound salt-containing aqueous solution or adding the both into a separate reaction bath.

Regarding mixing of the fatty acid-alkaline compound salt-containing aqueous solution and the magnesium salt-containing aqueous solution, when the magnesium salt-containing aqueous solution is fed into the fatty acid-alkaline compound salt-containing aqueous solution at once, for example, the shapes of the obtained fatty acid magnesium salt particles may become ununiform, and the aspect ratio of the particles may become large. Thus, in the invention, the magnesium salt-containing aqueous solution is preferably dropped gradually at an appropriate speed to the fatty acid-alkaline compound salt-containing aqueous solution.

The concentration of the fatty acid-alkaline compound salt during the production of the fatty acid magnesium salt is generally 1 mass % to 20 mass %, preferably 5 mass % to 15 mass % in view of the productivity of the fatty acid magnesium salt and in view of the handling property of the fatty acid-alkaline compound salt-containing aqueous solution or the obtained fatty acid magnesium salt slurry. The concentration of the fatty acid-alkaline compound salt is preferably 1 mass % or more because the productivity of the fatty acid magnesium salt is excellent. When the concentration is 20 mass % or less, the viscosity of the fatty acid-alkaline compound salt-containing aqueous solution or the obtained fatty acid magnesium salt slurry does not increase, and uniform reaction is possible. Here, the concentration of the magnesium salt in the magnesium salt-containing aqueous solution is generally 10 mass % to 50 mass %, preferably 10 mass % to 40 mass % in view of the productivity of the fatty acid magnesium salt and in view of the handling property of the fatty acid-alkaline compound salt-containing aqueous solution or the obtained fatty acid magnesium salt slurry.

The reaction of the fatty acid-alkaline compound salt and the magnesium salt is conducted under the temperature conditions which one skilled in the art generally uses considering the solubility of the fatty acid-alkaline compound salt. The temperature is preferably 50 to 100° C., more preferably 60 to 95° C. When the reaction temperature is 50° C. or higher, the reaction rate of the fatty acid-alkaline compound salt and the magnesium salt is excellent.

For the purpose of stabilizing the fatty acid magnesium salt slurry and improving the productivity of the fatty acid magnesium salt during the reaction of the fatty acid-alkaline compound salt and the magnesium salt, a polyalkylene glycol ether, especially a triblock ether having a structure in which an oxypropylene block is between oxyethylene blocks (EO-PO-EO), is preferably contained in the fatty acid magnesium salt slurry. The polyalkylene glycol ether content of the fatty acid magnesium salt slurry is generally 0.01 parts by mass to 5 parts by mass, preferably 0.05 parts by mass to 2 parts by mass based on 100 parts by mass of the fatty acid-alkaline compound salt. The polyalkylene glycol ether may be contained in the reaction system before the reaction of the monovalent alkaline compound and the fatty acid and may also be contained in the reaction system before the reaction of the fatty acid-alkaline compound salt and the magnesium salt.

A fatty acid magnesium salt cake with a water content that is reduced through separation with one dehydrator, a filter press or the like is obtained by the method. The fatty acid magnesium salt cake with a reduced water content is dried with a rotary dryer, a flash dryer, a ventilated tray dryer, a vacuum tray dryer, a spray dryer, a fluidized bed dryer or the like.

In the invention, it is necessary that the fatty acid magnesium salt cake is dried at $(\alpha-60)°$ C.$\leq\alpha\leq(\alpha-30)°$ C. regarding the contained water evaporation peak top temperature ($\alpha°$ C.) of the produced fatty acid magnesium salt. Here, the contained water evaporation peak top temperature is the top peak of the peak in the temperature range in which the residual water contained in the fatty acid magnesium salt which cannot be removed by the drying starts to desorb, and for example, the contained water evaporation peak top temperature is 102.1° C. in the heat absorption graph of magnesium myristate by differential thermal analysis (DSC) in FIG. 1. The specific drying temperature differs with the kind of the obtained fatty acid magnesium salt but is 72° C. or lower in the case of magnesium myristate, for example. When the drying treatment is conducted at a temperature higher than 72° C., the microparticles adhere to each other, and the particle thickness is apt to be large. On the other hand, when the drying treatment is conducted at a temperature lower than 40° C., the drying property decreases, and a large amount of water remains in the compound. The productivity may thus decrease.

The aspect ratio of the fatty acid magnesium salt particles of the invention is 1.0 or more and 2.0 or less, preferably 1.0 or more and 1.6 or less, more preferably 1.0 or more and 1.5 or less.

In the invention, the aspect ratio of a particle corresponds to the following formula (1), namely the value obtained by dividing the major axis diameter of a fatty acid magnesium salt particle by the minor axis diameter (=major axis diameter/minor axis diameter).

$$\text{Aspect Ratio}=\text{Major axis diameter of Particle } (\mu\text{m})/\text{Minor axis diameter of Particle } (\mu\text{m}) \qquad \text{formula (1)}$$

An aspect ratio which is closer to 1.0 means that the shape of the particle is closer to a square or a circle. The fatty acid magnesium salt particles of the invention preferably have a shape which is close to a square. As a result, spreading on the skin improves, and the use feeling is excellent.

Here, the "major axis diameter" of a particle is the length of the major axis of the particle and more specifically corresponds to the width of the particle where the distance between two parallel lines sandwiching the particle becomes the maximum. The "minor axis diameter" of the particle is the length of the minor axis of the particle and more specifically corresponds to the width of the particle measured on the straight line which passes through the midpoint of the major axis and which intersects the major axis at right angles. Here, the average thickness of particles is the average determined by measuring the lengths of side faces of 10 particles while setting the faces of the fatty acid magnesium salt particles with the largest areas as front faces. The average thickness of the particles is a value measured based on two-dimensional projection images of the particles (specifically, SEM images).

The average thickness of the fatty acid magnesium salt particles of the invention is 250 to 600 nm. Due to the thickness, the particles easily dissolve even under mild mixing conditions (production method) for the cosmetic. Moreover, the cosmetic is easily applied to the skin evenly, and the texture after the application can also be improved. When the average thickness is 250 nm or more, the handling property of the fatty acid magnesium salt particles is excellent during the addition to the cosmetic, and there is no risk of reduction in the workability. The average thickness of the particles is more preferably 280 to 450 nm, particularly preferably 300 to 450 nm. When the average thickness of 300 to 450 nm is satisfied, the effects of action of the invention are obtained further more stably.

The particle index of the fatty acid magnesium salt particles of the invention is preferably 1.5 or more and 8.0 or less. Due to the particle index, the cosmetic is easily applied to the skin evenly, and the texture after the application can be maintained for a long time. When the particle index is 1.5 or more, the dispersibility of the fatty acid magnesium salt particles is excellent during the addition to the cosmetic, and there is no risk of reduction in the workability. The particle index of the particles is preferably 1.5 or more and 6.0 or less, more preferably 2.0 or more and 5.0 or less. When the particle index of 2.0 or more and 5.0 or less is satisfied, the effects of action of the invention are obtained further more stably.

Here, in the invention, the particle index of the particles corresponds to the following formula (2), namely the value obtained by dividing the value obtained by dividing the major axis diameter of the fatty acid magnesium salt particles by the minor axis diameter (=major axis diameter/minor axis diameter) by the average thickness of the particles [=(major axis diameter/minor axis diameter)/average thickness of particles].

$$\text{Particle Index}=[(\text{Major axis diameter of Particles } (\mu\text{m})/\text{Minor axis diameter of Particles } (\mu\text{m}))/\text{Average Thickness of Particles } (\text{nm})]\times 1000 \qquad \text{formula (2)}$$

The fatty acid magnesium salt particles of the invention have a narrow particle size distribution and thus can uniformly exist in the cosmetic, and the effects of action of the invention (especially the improvement of the texture of the cosmetic) are exhibited more stably. Specifically, the median size of the fatty acid magnesium salt particles is preferably 10.0 to 40.0 μm and the particle size digest A expressed by the following formula (3) is preferably 2.5 or less.

$$\text{Particle Size Digest } A=(D90-D10)/D50 \qquad \text{formula (3)}$$

(Here, $10.0\leq D50\leq 40.0$.)

D10: the 10% cumulative size (μm) of the fatty acid magnesium salt particles on a volumetric basis D50: the median size (μm) of the fatty acid magnesium salt particles on a volumetric basis D90: the 90% cumulative size (μm) of the fatty acid magnesium salt particles on a volumetric basis In the invention, the particle size digest A is calculated from the particle sizes measured by the Microtrac laser diffraction method. When the particle size digest A is 2.5 or less, the fatty acid magnesium salt particles in the cosmetic have a uniform particle size, and the dispersibility of the cosmetic is excellent. Moreover, the productivity does not decrease, and a cosmetic having an aimed texture can be produced. The particle size digest A more preferably satisfies the relation $0.5\leq A\leq 2.5$. When the relation $0.5\leq A\leq 2.5$ is satisfied, the effects of action of the invention are obtained further more stably. When the particle size digest A is 0.5 or more, the yield does not decrease, and industrially stable production is possible.

Here, when a cumulative curve is drawn in which the total volume of the powder population is regarded as 100% in the formula (3), the particle sizes at 10%, 50% and 90% of the cumulative curve are referred to as the 10% cumulative size (D10), the 50% median size (D50; median size) and the 90% cumulative size (D90) (μm), respectively. Here, the particle size means the particle size of a primary particle. When the particles cohere during the measurement, the particles are measured in a state of being dispersed with ultrasonic wave or the like.

The particle size digest A can be adjusted by appropriately adjusting the concentration of the fatty acid-alkaline compound salt, the temperature of the reaction of the fatty acid-alkaline compound salt and the magnesium salt and the dropping speed for dropping the magnesium salt-containing aqueous solution to the fatty acid-alkaline compound salt-containing aqueous solution. Moreover, when the particles have a broad particle size distribution, namely, a large particle size digest A value, the particle size digest A can be adjusted through sorting using a sieve such as 100 mesh, 200 mesh and 330 mesh in the posttreatment.

The Microtrac laser diffraction method used here is a method for determining the particle size distribution using scattered light obtained by irradiating particles with laser beam. In the invention, the measurement is made by the wet method in which the sample is fed while an organic solvent into which the fatty acid magnesium salt particles do not dissolve, such as organic solvents including ethanol, isopropyl alcohol and the like, circulates. Moreover, the measurement target in the invention has a particle size in the range of 0.1 μm to 200 μm, and the value expressed by the formula (3) is the particle size digest A. In the invention, the measurement can be made, for example, using Microtrac MT-3000 manufactured by Nikkiso Co., Ltd.

The median size (D50) of the fatty acid magnesium salt particles of the invention on a volumetric basis is preferably 10.0 to 40.0 μm. Due to the particle size, the texture upon use is excellent. The median size of the fatty acid magnesium salt particles is preferably 13.0 to 35.0 μm, more preferably 15.0 to 25.0 μm. The particle size can be measured by the Microtrac laser diffraction method like the particle size digest A described above.

To obtain the fatty acid magnesium salt particles which satisfy the specific properties, when a magnesium salt-containing aqueous solution and a fatty acid-alkaline compound salt-containing aqueous solution which are prepared separately by metathesis reaction are mixed, the magnesium salt-containing aqueous solution is preferably dropped gradually into the fatty acid-alkaline compound salt-containing aqueous solution. The dropping speed is preferably 0.005 to 0.8 mol/minute per unit time, further preferably 0.01 to 0.5 mol/minute. By mixing at the dropping speed, the exchange reaction of the alkali and the magnesium can be advanced gently, and fatty acid magnesium salt particles having a moderate aspect ratio and a moderate thickness can be obtained. When the speed is 0.005 mol/minute or more, fatty acid magnesium salt particles having a desired aspect ratio and a desired thickness can be obtained. On the other hand, when the dropping speed per unit time is 0.8 mol/minute or less, the fatty acid magnesium salt particles have a uniform shape, and the particles have a desired aspect ratio and a desired thickness. Thus, the particle size is not uneven, which is excellent.

The unit of the magnesium salt dropped, "mol/minute", is the number of moles of the magnesium salt dropped per 1 mole of the fatty acid-alkaline compound per unit time.

The shape of the fatty acid magnesium salt particles of the invention is not particularly limited but is preferably plate-like in view of the use feeling.

The cosmetics for which the fatty acid magnesium salt particles of the invention can be used include skin care cosmetics such as facial washing cream, face lotion, massage cream, milky lotion and moisture cream, makeup cosmetics such as foundation, eye shadow, eye liner, lipsticks and blush, body care cosmetics such as bath products, sunscreen creams and deodorant spray, hair care cosmetics such as shampoo, conditioner, hair liquids and hair dyes and the like.

In addition to the fatty acid magnesium salt particles of the invention, as other known cosmetic materials, organic pigments, inorganic pigments, fragrance, oils and fats, waxes, hydrocarbons, higher fatty acids, higher alcohols, esters, silicone oils, nonionic, anionic, cationic and amphoteric surfactants, other surfactants, moisturizing agents, ultraviolet absorbers, antioxidants and the like can be used.

EXAMPLES

The invention is explained further specifically below referring to Examples and Comparative Examples.

Preparation of Fatty Acid Magnesium (Magnesium Myristate) Salt Particles

Example 1

Into a 3-L separable flask, 200 g of myristic acid (NAA-142 manufactured by NOF Corporation), 1.00 g of polyethylene glycol/polypropylene glycol block ether (manufactured by NOF Corporation, product name: Plonon #104) and 2500 g of water were charged, and the temperature was increased to 80° C. Next, 73.6 g of 48 mass % aqueous sodium hydroxide solution was added and stirred at the same temperature (80° C.) for 30 minutes, and thus an aqueous sodium myristate solution was obtained. Then, while maintaining at 80° C., 253.8 g of 22 mass % aqueous magnesium sulfate solution was dropped to the aqueous sodium myristate solution over 40 minutes [dropping speed: 0.013 (mol/minute)]. After the completion of dropping, the mixture was maintained at 80° C. and stirred for 30 minutes for aging. The obtained aqueous fatty acid magnesium salt solution slurry was left to cool to 60° C. or lower. Then, the mixture was filtered with a suction filter, followed by washing twice with 1000 g of water, and the obtained cake was dried at 60° C. using a ventilated tray dryer and crushed in a mill. Thus, magnesium myristate particles were obtained.

Example 2

Into a 6-L separable flask, 220 g of myristic acid (NAA-142 manufactured by NOF Corporation), 1.10 g of polyethylene glycol/polypropylene glycol block ether (manufactured by NOF Corporation, product name: Plonon #104) and 2400 g of water were charged, and the temperature was increased to 85° C. Next, 80.1 g of 48 mass % aqueous sodium hydroxide solution was added and stirred at the same temperature (85° C.) for 30 minutes, and thus an aqueous sodium myristate solution was obtained. Then, while maintaining at 85° C., 330.0 g of 22 mass % aqueous magnesium sulfate solution was dropped to the aqueous sodium myristate solution over 60 minutes [dropping speed: 0.010 (mol/minute)]. After the completion of dropping, the mixture was maintained at 80° C. and stirred for 20 minutes for aging. The obtained aqueous fatty acid magnesium salt solution slurry was cooled to 65° C. or lower. Then, the mixture was filtered with a suction filter, followed by washing six times with 4000 g of water, and the obtained cake was dried at 60° C. using a ventilated tray dryer and crushed in a mill. Thus, magnesium myristate particles were obtained.

Example 3

Into a 10-L separable flask, 500 g of myristic acid (NAA-142 manufactured by NOF Corporation) and 5600 g of water were charged, and the temperature was increased to 90° C. Next, 250.0 g of 48 mass % aqueous sodium hydroxide solution was added and stirred at the same temperature (90° C.) for an hour, and thus an aqueous fatty acid-alkaline compound salt solution was obtained. Then, while maintaining at 90° C., 750.0 g of 22 mass % aqueous magnesium sulfate solution was dropped to the aqueous sodium myristate solution over 40 minutes [dropping speed: 0.016 (mol/minute)]. After the completion of dropping, the mixture was maintained at 90° C. and stirred for 30 minutes for aging. The obtained aqueous fatty acid magnesium salt solution slurry was cooled to 65° C. or lower. Then, the mixture was filtered with a suction filter, followed by washing eight times with 1000 g of water, and the obtained cake was dried at 60° C. using a ventilated tray dryer and crushed in a mill. Thus, magnesium myristate particles were obtained.

Comparative Example 1

Into a 3-L separable flask, 200 g of myristic acid (NAA-142 manufactured by NOF Corporation), 1.00 g of polyethylene glycol/polypropylene glycol block ether (manufactured by NOF Corporation, product name: Plonon #104) and 2500 g of water were charged, and the temperature was increased to 60° C. Next, 73.6 g of 48 mass % aqueous sodium hydroxide solution was added and stirred at the same temperature (60° C.) for 30 minutes, and thus an aqueous sodium myristate solution was obtained. Then, while maintaining at 60° C., 253.8 g of 22 mass % aqueous magnesium sulfate solution was fed into the aqueous sodium myristate solution [dropping speed: 10.59 (mol/minute)]. After the completion of dropping, the mixture was maintained at 60° C. and stirred for 30 minutes for aging. The obtained aqueous fatty acid magnesium salt solution slurry was filtered with a suction filter, followed by washing twice with 1000 g of water, and the obtained cake was dried at 60° C. using a ventilated tray dryer and crushed in a mill. Thus, magnesium myristate particles were obtained.

Comparative Example 2

Into a 5-L separable flask, 500 g of myristic acid (NAA-142 manufactured by NOF Corporation) and 3000 g of water were charged, and the temperature was increased to 60° C. under stirring. Next, 43 g of magnesium hydroxide was added at the same temperature over 30 minutes. After the completion, the temperature was increased to 90° C., and stirring was continued for an hour. Thus, a magnesium myristate slurry was obtained. The magnesium myristate slurry was cooled to 60° C. and then filtered using a suction filter, and then the obtained cake was dried at 50° C. using a ventilated tray dryer and pulverized in a mill. Thus, magnesium myristate particles were obtained.

Comparative Example 3

Into a 3-L separable flask, 200 g of myristic acid (NAA-142 manufactured by NOF Corporation), 1.00 g of polyethylene glycol/polypropylene glycol block ether (manufactured by NOF Corporation, product name: Plonon #104) and 2500 g of water were charged, and the temperature was increased to 80° C. Next, 73.6 g of 48 mass % aqueous sodium hydroxide solution was added and stirred at the same temperature (80° C.) for 30 minutes, and thus an aqueous sodium myristate solution was obtained. Then, while maintaining at 80° C., 253.8 g of 22 mass % aqueous magnesium sulfate solution was dropped to the aqueous sodium myristate solution over 40 minutes [dropping speed: 0.013 (mol/minute)]. After the completion of dropping, the mixture was maintained at 80° C. and stirred for 30 minutes for aging. The obtained aqueous fatty acid magnesium salt solution slurry was left to cool to 60° C. or lower. Then, the mixture was filtered with a suction filter, followed by washing twice with 1000 g of water, and the obtained cake was dried at 105° C. using a ventilated tray dryer and crushed in a mill. Thus, magnesium myristate particles were obtained.

The median sizes, the particle size digests A [the values calculated from the 10% cumulative size D10 (μm) on a volumetric basis, the median size D50 (μm) on a volumetric basis and the 90% cumulative size D90 (μm) on a volumetric basis], the thicknesses of the particles, the major axis diameters and the minor axis diameters of the magnesium myristate particles of Examples 1 to 3 and Comparative Examples 1 to 3 were measured using the following devices by the methods described above. The results are shown in Table 1.

(1) Particle Size Digest A and Median Size

A sample in an amount of 2.0 g was taken in a 100-ml glass beaker, and 3 to 5 ml of a nonionic surfactant (example; Nonion NS-210 manufactured by NOF Corporation) was dropped and blended with a spatula. Next, 20 ml of purified water was added, and the sample was dispersed by ultrasonic wave. The volume was adjusted to 100 ml, and thus a measurement sample was obtained. The sample was fed to and measured with a particle size distribution analyzer (machine name "Microtrac MT-3000" manufactured by Nikkiso Co., Ltd.) (principle: laser diffraction/scattering method).

A cumulative curve was drawn in which the total volume of the powder population measured was regarded as 100%, and the particle sizes at 10%, 50% and 90% of the cumulative curve were determined as the 10% size (D10), the 50% size (D50; median size) and the 90% size (D90) (μm), respectively. The particle size digest A was determined from the obtained D10, D50 and D90.

(2) Average Thickness of Particles, Major Axis Diameter, Minor Axis Diameter, Aspect Ratio and Particle Index The thickness of the particles was measured by the following method using a scanning electron microscope. A sample obtained by adhering fatty acid magnesium salt particles on a double-sided carbon tape and then coating the particle surfaces with platinum particles by vapor deposition was observed at an acceleration voltage of 1.0 kV and at 2000× magnification, and the thicknesses of particles were measured at random. The thicknesses, the major axis diameters and the minor axis diameters of 10 particles at random were determined. Moreover, the aspect ratio and the particle index were determined by the following formulas.

$$\text{Particle Index}=[(\text{Major axis diameter }(\mu m)/\text{Minor axis diameter }(\mu m))/\text{Average Thickness of Particles }(nm)]\times 1000$$

$$\text{Aspect Ratio}=\text{Major axis diameter }(\mu m)/\text{Minor axis diameter }(\mu m)$$

Pictures of the fatty acid magnesium salt particles of Examples 1 and 3 and Comparative Examples 1 to 3 observed under a scanning electron microscope are shown in FIGS. 2 to 6.

[Assessment of Use Feeling]

The textures upon use and the like of the fatty acid magnesium salt particles obtained by the invention were assessed based on the following criteria. The results are shown in Table 1.

(Smoothness)

Two expert analysts determined the smoothness of the fatty acid magnesium salt particles when the particles were applied to the skin as follows, and the smoothness was determined to be excellent in the case of A or B.

A: very smooth
B: smooth
C: not so smooth
D: not smooth (Luster)

Two expert analysts determined the luster on the skin of the fatty acid magnesium salt particles when the particles were applied to the skin as follows, and the luster was determined to be excellent (the particles had luster) in the case of A or B.

A: having strong luster
B: having luster
C: having little luster
D: having no luster (Transparency)

Two expert analysts determined the transparency of the fatty acid magnesium salt particles when the particles were applied to the skin as follows, and the transparency was determined to be excellent in the case of A or B.

A: very high transparency
B: high transparency
C: slightly low transparency
D: low transparency

[Table 1]

TABLE 1

| | | Example 1 | Example 2 | Example 3 | Comparative Example 1 | Comparative Example 2 | Comparative Example 3 |
|---|---|---|---|---|---|---|---|
| Particle Properties | D10 (μm) | 9.8 | 9.5 | 11.4 | 3.0 | 4.7 | 1.4 |
| | D50 (median size) (μm) | 19.1 | 18.6 | 25.3 | 5.9 | 13.6 | 5.3 |
| | D90 (μm) | 34.0 | 34.4 | 54.9 | 9.7 | 42.3 | 34.2 |
| | Aspect Ratio (major axis diameter/minor axis diameter) | 1.0 | 1.2 | 1.4 | 3.4 | 1.2 | 1.4 |
| | Average Thickness of Particles (nm) | 424 | 370 | 309 | 343 | 1085 | 996 |
| | Particle Index (major axis diameter/minor axis diameter/thickness) | 2.4 | 3.2 | 4.7 | 10.0 | 1.1 | 1.4 |
| | Particle Size Digest A | 1.3 | 1.3 | 1.7 | 1.1 | 2.8 | 6.2 |
| Assessment of Use Feeling | Smoothness | A | A | A | B | B | D |
| | Luster | A | B | B | D | D | C |
| | Transparency | A | A | A | C | C | D |

As shown in Table 1, the results of the fatty acid magnesium salt particles of Examples 1 to 3, in which the aspect ratios and the average thicknesses of the particles were in specific ranges, were excellent in all the items of smoothness, luster and transparency, and it is seen that the fatty acid magnesium salt particles had excellent use feeling. On the other hand, the results of the fatty acid magnesium salt particles of Comparative Examples 1 to 3, in which the aspect ratios and the average thicknesses of the particles did not satisfy the specific ranges, did not meet the criteria in some of the items of smoothness, luster and transparency.

<Formulation Example: Face Powder>

A formulation example of a face powder containing the fatty acid magnesium salt particles of the invention is shown in Table 2 below.

[Table 2]

TABLE 2

| Material Name | Formulation Example |
|---|---|
| Magnesium Myristate (Example 1) | 10.00 |
| Talc | to 100% |

TABLE 2-continued

| Material Name | Formulation Example |
|---|---|
| Silicone-Treated Red Iron Oxide | 0.50 |
| Silicone-Treated Ocher | 0.80 |
| Spherical Silica | 6.00 |
| Preservative | Moderate Amount |
| Dimethicone Oil | 2.00 |
| Phenyldimethicone Oil | 4.00 |
| Vaseline | 2.00 |
| Sorbitan Sesquiisostearate | 0.50 |
| Total (mass %) | 100.00 |

Although the invention has been explained in detail referring to specific embodiments, it is obvious to one skilled in the art that various changes and modifications can be made without departing from the spirit and the scope of the invention. The present application is based on a Japanese patent application filed on Sep. 30, 2020 (patent application No. 2020-164351), and the contents thereof are incorporated here by reference.

INDUSTRIAL APPLICABILITY

The fatty acid magnesium salt particles of the invention have excellent use feeling such as smoothness, luster and transparency and thus are suitable as an additive for cosmetics such as foundation and face powder.

The invention claimed is:

1. Particles consisting of a magnesium salt of a fatty acid wherein the fatty acid has 12 to 22 carbon atoms, each of the particles has a plate shape;

an average thickness of the particles is 300 to 450 nm, and an aspect ratio of the particles is at least 1.0 and no greater than 1.5, wherein the aspect ratio is a ratio of a major axis diameter of a particle in a plane perpendicular to a thickness direction of the particle to a minor axis of the particle in the plane perpendicular to the thickness direction of the particle.

2. The particles according to claim 1, wherein the median size of the particles is 10.0 μm to 40.0 μm.

3. The particles according to claim 1, wherein a particle size digest (A) expressed by the following formula (3) satisfies the relation $A \leq 2.5$, wherein the formula (3) is the particle size digest $A=(D90-D10)/D50$, wherein $10.0 \leq D50 \leq 40.0$, wherein D10 is a 10% cumulative size (μm) of the particles on a volumetric basis, D50 is a median size (μm) of the particles on a volumetric basis, and D90 is a 90% cumulative size (μm) of the particles on a volumetric basis.

4. The particles according to claim 1, wherein the fatty acid having 12 to 22 carbon atoms is myristic acid.

5. A cosmetic containing the particles according to claim 1.

6. The particles according to claim 1, wherein the particles are prepared by (a) preparing separately a first aqueous solution comprising a magnesium salt and a second aqueous solution comprising an alkaline compound salt of the fatty acid separately and (b) mixing the first solution and the second solution by gradually adding the first solution to the second solution.

* * * * *